US006726932B2

(12) United States Patent
Konishi

(10) Patent No.: US 6,726,932 B2
(45) Date of Patent: Apr. 27, 2004

(54) FATTY ACID-CONTAINING COMPOSITION

(75) Inventor: Jin-emon Konishi, Osaka (JP)

(73) Assignee: Nippon Zoki Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/788,007

(22) Filed: Feb. 16, 2001

(65) Prior Publication Data

US 2003/0018011 A1 Jan. 23, 2003

(30) Foreign Application Priority Data

Feb. 18, 2000 (JP) ........................................ 2000-041327

(51) Int. Cl.$^7$ ................................................. A61K 9/14
(52) U.S. Cl. ........................ 424/489; 424/451; 424/464; 424/422; 424/484; 424/486; 424/499; 424/501; 424/502; 424/78.08
(58) Field of Search ............................. 424/78.08, 422, 424/484, 486, 489, 499, 501, 502, 451, 464

(56) References Cited

U.S. PATENT DOCUMENTS

| 3,959,566 A | 5/1976 | Pangonis |
| 4,036,787 A | 7/1977 | Blount |
| 4,039,474 A | 8/1977 | Feistel et al. |
| 4,056,937 A | 11/1977 | Suzuki |
| 4,089,883 A | 5/1978 | Blount |
| 4,138,421 A | 2/1979 | Blount |
| 4,145,415 A | 3/1979 | Sato |
| 4,640,361 A | 2/1987 | Smith et al. |
| 4,863,518 A | 9/1989 | Blount |
| 4,879,297 A | 11/1989 | Mahjour et al. |
| 4,985,254 A | 1/1991 | Konishi |
| 4,985,354 A | 1/1991 | Toyomaki et al. |
| 5,013,558 A | 5/1991 | Konishi |
| 5,057,324 A | 10/1991 | Shibayama et al. |
| 5,127,994 A | 7/1992 | Johansson |
| 5,227,089 A | 7/1993 | Hasegawa et al. |
| 5,523,295 A | 6/1996 | Fasman |
| 5,534,509 A | 7/1996 | Konishi et al. |
| 5,560,935 A | 10/1996 | Konishi et al. |
| 5,576,025 A * | 11/1996 | Akiyama et al. ........... 424/501 |
| 5,658,896 A | 8/1997 | Konishi et al. |
| 5,767,103 A | 6/1998 | Greenberg et al. |
| 5,807,951 A * | 9/1998 | Konishi et al. ............. 527/300 |
| 6,051,613 A | 4/2000 | Ohno et al. |
| 6,165,515 A | 12/2000 | Matsuyama et al. |
| 6,365,192 B1 | 4/2002 | Konishi |

FOREIGN PATENT DOCUMENTS

| EP | 0 300 973 | 1/1989 |
| EP | 0 315 591 A2 | 5/1989 |
| EP | 0 341 209 A2 | 11/1989 |
| EP | 0 348 353 A2 | 12/1989 |
| EP | 0 621 038 A1 | 10/1994 |
| EP | 0 645 142 A1 | 3/1995 |
| EP | 0 733 636 A1 | 9/1996 |
| EP | 0 919 238 A3 | 6/1999 |
| EP | 0 953 352 A1 | 11/1999 |
| FR | 2 610 523 | 8/1988 |
| FR | 2 671 488 | 7/1992 |
| FR | 2 720 068 | 11/1995 |
| GB | 697351 | 9/1953 |
| JP | 53-101515 | 9/1978 |
| JP | 57-77697 | 5/1982 |
| JP | 57-183720 | 11/1982 |
| JP | 58-35117 | 3/1983 |
| JP | 58-121217 | 7/1983 |
| JP | 62-145022 | 6/1987 |
| JP | 2-73020 | 3/1990 |
| JP | 3-43279 | 7/1991 |
| JP | 3-204803 | 9/1991 |
| JP | 2594222 | 12/1996 |
| JP | 63-25600 | 5/1998 |
| JP | 63-039572 | 8/1998 |
| WO | WO 93/08828 | 5/1993 |
| WO | WO 97/05903 A | 2/1997 |
| WO | WO 98/13377 | 4/1998 |

OTHER PUBLICATIONS

Yokoi, et al., "Effect of Degree of Polymerization of Silicic Acid on the Gastrointestinal Absorption of Silicate in Rats", Chem. Pharm. Bull., vol. 27, No. 8, 1979, pp. 1733–9.
The Merck Index, Ninth Edition, Nos. 7456,8443,8232–8243, and 5514–5515 (1976).
Database Biosis, XP–002113089, Li S–Y et al., Studies on the Protective Action of Silicon Compound of Equisetum Against Experimental Liver Injury in Rats and Mice & Zhongguo Yaolixue Yu Dulixue Zazhi. ISSN: 1000–3002, abstract.

(List continued on next page.)

Primary Examiner—Thurman K. Page
Assistant Examiner—Liliana Di Nola-Baron
(74) Attorney, Agent, or Firm—Hollander Law Firm, P.L.C.

(57) ABSTRACT

The present invention provides a composition for enhancing the pharmacological activity of a water-soluble silicate polymer which comprises the water-soluble silicate polymer and a saturated fatty acid in pharmaceutically effective amounts for use as a medicine such as anti-allergic agent. The water soluble silicate polymers used according to the present invention may be obtained by polymerization and/or by extraction from plants, animals or fungi, or inflammatory tissue. The saturated fatty acid contained as an effective ingredient in the pharmaceutical composition of the present invention may be a straight chain or branched chain saturated fatty acid having about 8 carbon atoms to about 26 carbon atoms. The saturated fatty acid and water-soluble silicate polymer, effective ingredients of the present invention, can be formulated for various pharmaceutical compositions by combining with a suitable carrier or diluent for medical use. The composition of the present invention can suppress histamine release induced by a structural change in the cell membrane of the mast cell. It exhibits an excellent organism maintaining function such as cell protecting action and, therefore, is useful as a medicine such as an anti-allergic or anti-inflammatory agent.

27 Claims, No Drawings

OTHER PUBLICATIONS

Zhao, C., et al., "Determination of water soluble silicon from herbal drugs", Chung Kuo Chung Yao Tsa Chih, vol. 15, No. 9, 1990, pps. 555–556.

Paslawska et al., "Studies on the Optimum Conditions of Extraction of Silicon Species from Plants With Water", Planta Medica, vol. 29, No. 1, 1976, pps. 72–79, & XP002113087.

Piekos et al., "Studies on the Optimum Conditinos of Extraction of Silicon Species from Plants With Water", Planta Medica, vol. 27, 1975, pps. 145–150, XP002113088.

Webster's New world Dictionary $3^{rd}$, 1988, Ed., Neufeldt & Gurainik Infarct, p. 691.

Webster's New World Dictionary, $3^{rd}$, Definitions of embolism, infarct, ischemia, hypoxia and thrombosis.

Database WPI, Section Ch, Week 9411, Derwent, XP002113091 & RU 2003338 C, Nov. 30, 1993, abstract.

Takeoka, Y. et al., "Influence of Neurotropin on Thymic Microenviromental Abnormalities of NZB Mice," Int. J. Immunotherapy, XI(2), pp. 49–56 (1995).

"Drugs in Japan, Ethical Drugs," Yakugyo Jiho Co., Ltd., 1994, p. 1434.

Fujii, Y., et al., "Biological Overview of HIV Accessory Protein Nef," Saibo Kogaku, vo. 16, No. 1, pp. 94–99 (1997).

Section CH, Week 9645, Derwent Publications Ltd., Class B04, AN 96–450925 XP002109698 & JP 08 225452 A, Sep. 3, 1996, abstract.

De Reuck J., et al., "A double–blind study of neurotropin in patients with acute ischemic stroke," ACTA Neurologica Scandinavica vol. 89, No. 5, 1994, pps. 329–335, XP002109696.

Sprumont, et al., "Morphometrical Quantification of Brain Edema Related to Experimental Multiple Micro–Infarcts in Mice: Assessment of Neurotropin Effect," Meth Find Exp Clin Pharmacol 1993, 15(3): 169–177, XP002109697.

Tanaka et al., Int. Clin. Psychopharm., 3(3):239–44, Medline Abst. No. 91079456 (Jul. 1988).

Donnelly et al., Am. J. Physiol., 262 (5 Pt 1):L549–554, Medline Abst. No. 92272204 (May 1992).

Okada H., et al., "Inhibition of HIV—1 Nef induced apoptosis of uninfected human blood cells by serine/threonine protein kinase inhibitors, fasudil hydrochloride and M3" Febs Letters, vol. 422, No. 3, 1998, pps. 363–367, XP002115665, Amsterdam, NL.

Luo T., et al., "Infectivity enhancement by immunodeficiency virus type 1 Nef is independent of its association with a cellular serine/threonine kinase" Journal of Virology, vol. 71, No. 12, 1997, pps. 9524–9530, XP00211566 US.

Rossi F., et al., "HsN3 proteasomal subunit as a target for human immunodeficiency virus type 1 Nef protein" Virology, vol. 237, No. 1, 1997, pps. 33–45, XP002115667, Orlando, US.

Smith, B.L. et al., "The HIV Nef protein associates with protein kinase C theta" Journal of Biological Chemistry, vol. 271, No. 28, pps. 16753–16757, XP002115668, MD US.

Fahey et al., "Status of Immune–based therapies in HIV infection and AIDS," Clin. Exp. Immunol. (1992) 88, 1–5.

Fundamental Immunology/Immunodeficiency, Third Edition, W. E. Paul, Editor, Raven Press, 1993, pps. 1354–1369.

Liu et al., "Binding of HIV-1 Nef to a novel thioesterase enzyme correlates with Nef–mediated CD4 down–regulation." The Journal of Biological Chemistry, vol. 272 (1997) pps. 13779–13785.

Piguet V., "The Nef protein of primate lentiviruses," Rev Med Viro 9(2):111–20 Apr.–Jun. 1999, abstract.

Mandell CP., "SIV/HIV Nef recombinant virus (SHIV nef) produces simian AIDS in rhesus macaques" Virology, 265 (2):235–51 Dec. 20, 1999 abstract.

Chemical Abstracts, vol. 106, No. 10, Mar. 9, 1987, Srivastava et al., XP002096181.

Patent Abstracts of Japan, vol. 017, No. 225 (C–1055), May 10, 1993 & JP 04360838.

Database WPI Section CH, Week 9624, Derwent, XP002113090 & CN 1 096 180, Dec. 14, 1994, abstract.

Wang et al., Mushroom Biology and Mushroom Products, Proc. Int. Conf. 2nd, Editor: Royse, Daniel J., Publisher: Penn State University, College of Agricultural Sciences, University Park, PA, 1996, pps. 205–208.

Kinter, A., et al., 2000, "Chemokines, cytokines, and HIV: . . . ", Immunol. Rev. 177:88–98.

Murdoch, C. and A. Finn, 2000, "Chemokine receptors and their role . . . ", Blood 95(10):3032–3043.

Boltz et al., Analytical Chemistry (1947), vol. 19, No. 11, pp. 873–877.

Derwert abstract of SU 1833171 A3 (1993).

Steranka et al., "Brandykinin as a pain mediator: receptors are localized to sensory neurons, and antagonists have analgesic actions.", Proc Natl Acad Sci USA,, May 1988, 85(9):3245–9.

Galvez et al., "Antidiarrhoeic activity of Euphorbia hirta extract and isolation of an active flavonoid constituent.", Plant Med, Aug. 1993, 59(4):33–6.

Hamada et al., "Free radical scavenging action of baicalein.", Arch Biochem Biphys., Oct. 1993, 306(1):261–6.

Xu et al., "Immunological mechanisms of antitumor activity of some kinds of crude drugs on tumor necrosis factor production." Int J Immunopharmacol, 1989, 11(6):607–13.

Habib et al., "Difference spectrophotometric estimation of santonin", J Assoc Off Anal Chem, Sep.–Oct. 1984, 67(5):939–41.

Lin et al., "Medicinal plants used for the treatment of hepatitis in Taiwan", Am J Chin Med, 1990, 18(1–2):35–43.

Lin et al., "The anti–flammatory effects of Chinese crude drug prescriptions on experimental arthritis.", Am J. Chin Med, 1995, 23(2):145–52.

Methods in Plant Histology, Equisetum: How to Study?, 3 pages.

Seisjo et al., Annals of Emergency Medicine, Jun. 22, 1993(6):959–69.

Shimizu et al., Br. Res. Bull., Dec., 29, 1992(6):767–72.

Gabrielian, Japan J. Pharmacol., 60:51–54, 1992.

"Drugs For Cultivated Fish", Derwent; AN 82–10241J, & JP A57183720 (Mitani J.), Nov. 12, 1982, abst.

Patent Abstracts of Japan, "Remedy for Burn," vol. 7, No. 255 (C–189), Oct. 6, 1983, & JPA58121217 (Kagitani Takeo) Jul. 19, 1983, abst.

Patent Abstracts of Japan, "Adsorbent for Peroxylipid," vol. 15, No. 474 (C–890), Dec. 3, 1991 & JPA3204803 (Shisedo Co. Ltd.) Sep. 6, 1991, abst.

Hawley's Condensed Chemical Dictionary, Fourteenth Edition, pp. 539 and 451.

* cited by examiner

FATTY ACID-CONTAINING COMPOSITION

FIELD OF THE INVENTION

The present invention relates to a pharmaceutical composition containing a fatty acid and a water-soluble silicate polymer in a pharmaceutically effective amount for use as a medicine such as an anti-allergic agent. The present invention relates to a method of enhancing the activity of a water-soluble silicate polymer in a pharmaceutical composition by mixing a saturated fatty acid and a water-soluble silicate polymer.

BACKGROUND OF THE INVENTION

Every cell, which is the fundamental unit of the living body, is surrounded by membrane. The membrane is not only useful as a protective envelope so that the activity inside the cell can be normally carried out but also plays a role as a door for taking the nutrients therein and for excreting the waste products and also as a transmitter of information into and from the cell. In the cells of higher animals, organelles of an internal membrane system are present inside in addition to the surrounding cell membrane. Organelles have variously differentiated roles. For example, mitochondria have a function of energy production, catabolic metabolism, cell respiration, etc.; the lysosome carries out digestion of substances inside and outside the cells since it contains many hydrolases therein; the endoplasmic reticulum is a place where biosubstances such as protein and lipid are produced; and the Golgi apparatus carries out transport and secretion of the biosubstances synthesized in endoplasmic reticulum to the outside of the cells.

The main components of each of the plasma membrane of the cells and of the organelle membrane are polar lipids and membrane proteins. Most of the lipids contained in the biomembrane are phospholipids in which phosphatidylcholine (PC) and phosphatidylethanolamine (PE) occupy 60–90% thereof. When the fatty acid composition of the phospholipid in hepatic cells of rat was investigated, palmitic acid was 37% and stearic acid was 32% in the PC of the plasma membrane while, in PE, palmitic acid was 26% and stearic acid was 33%. In the PC and PE of mitochondria, the amount of palmitic acid was 27% in both phospholipids and that of stearic acid was 22% and 27%, respectively. As such, saturated fatty acids such as palmitic acid and stearic acid have been known as important constituent components for the biomembrane.

Silicon is a natural element which is widespread in organisms of the animal and plant kingdoms. In particular, it exists as silicate in animal tissues like hair, feather, bone and skin and is known as an essential element in osteogenesis. In animal tissues, it is involved in cross linkage of collagen tissues and comprises one of the components of acidic mucopolysaccharides. Silicon is thus an essential element for a living body. However, few pharmacological activities of the administration to animals are presently known, for example, immuno-suppressing activity through its anti-macrophage effect and antidiabetic activity. As a medicine, some silicates like magnesium silicate and aluminum silicate are just used as antacids.

The present inventor has previously carried out continued studies taking note of the functions and the pharmacological actions of silicic acid and silicon-containing compounds in vivo. With regard to silicate polymers, a water-soluble silicate polymer manufactured by polymerization of water-soluble silicic acids by a method originated by the present inventor has been found to have excellent actions whereby any abnormality of the nervous system, endocrine system and immune system caused by cellular dysfunction of the living body occurring in a diseased state is adjusted and repaired whereby biofunction can be normalized.

The above pharmacological activities are not available in the state of a monomer but they have been found to be exhibited by water-soluble silicate polymers. For example, a water-soluble silicic acid polymer and a method for manufacturing the polymer are disclosed in Japanese Patent 2,698,908 and its medical uses as an analgesic agent, anti-allergic agent, paresthesia improving agent, peripheral blood flow improving agent and anti-inflammatory agent are mentioned in Japanese Patents 2,588,109, 2,727,441, 2,727,442, 2,948,784 and 3,113,619, respectively, and corresponding U.S. Pat. Nos. 5,534,509, 5,658,896, and 5,807,951 each to Konishi et al. However, it is desirable to improve the pharmacological activity of the said silicate polymer.

The present inventor has further carried out a study for the above-mentioned water-soluble silicate polymer and, as a result, has found that an increased pharmacological activity of the said silicate polymer can be obtained from a combination of the water-soluble silicate polymer with a saturated fatty acid which is a main constituting component of the cell membrane whereupon the present invention has been achieved.

SUMMARY OF THE INVENTION

The present invention relates to a pharmaceutical composition which is useful as a medicine such as an anti-allergic agent or an anti-inflammatory agent, wherein a water-soluble silicate polymer and a saturated fatty acid are contained in a pharmaceutically effective amount. The present invention also provides a method for enhancing the activity of a water-soluble silicate polymer by adding a saturated fatty acid to a product containing the water-soluble silicate polymer. The water-soluble silicate polymers employed in the invention may have a molecular weight distribution in the range of about 4,800 to about 2,000,000, preferably about 13,000 to about 1,000,000, which distribution is unimodal and which is determined by gel-filtration, ultrafiltration, electrophoresis and the like. The degree of polymerization of the said silicate polymers may be in the range of about 75 to about 33,000, preferably about 210 to about 16,500, wherein the monomer unit is —($SiO_2$)—.

The saturated fatty acid contained as an effective ingredient in the pharmaceutical compositions of the present invention is a general name for a fatty acid having neither a double bond nor a triple bond in a molecule and is represented by the chemical formula $C_nH_{2n+1}COOH$. Preferably, it is a straight chain or branched chain saturated fatty acid having about 8 carbon atoms to about 26 carbon atoms. Such a fatty acid may be used solely or as a mixture of plural fatty acids. The acid may be used either in a free form or as a salt such as a sodium salt and potassium salt and it is preferred to use it in a water-soluble form.

For the purpose of making a pharmaceutical composition of the invention, an aqueous solution containing one or more water-soluble silicate polymers is preferably dried to a powder. The pharmaceutical compositions of the present invention may be formed by a method of adding a solution of the saturated fatty acid to the water soluble silicate polymer to form a solution. By this method, the pharmacological activity of a water soluble silicate polymer or polymers is greatly increased with respect to treatment of allergies and inflammation. The saturated fatty acid and water-soluble silicate polymer, effective ingredients of the present invention, can be formulated for various pharmaceutical compositions by combining with a suitable carrier or diluent for medical use.

DETAILED DESCRIPTION OF THE INVENTION

The substance of the present invention comprises water soluble silicate polymers mixed with saturated fatty acids. The water soluble silicate polymers may be obtained by polymerization and/or by extraction from plants, animals or fungi. The water-soluble silicate polymer, one of the effective ingredients of the pharmaceutical composition of the present invention, may be produced by polymerization of silicic acids or silicates including orthosilicic acid, metasilicic acid, mesodisilicic acid, mesotrisilicic acid, mesotetrasilicic acid, etc. The silicates which may be used to produce the water-soluble silicate polymers of the present invention are the salts of silicic acids, for example, salts of silicic acids with alkali metals such as sodium and potassium. Materials containing silicic acid, for instance, water glass which is a concentrated aqueous solution of alkali salts of silicic acid, may also be used. Further, a silicate solution prepared by heating and dissolving silicon oxide in alkaline aqueous solution may be utilized. Examples of water-soluble sodium silicates which may be used to produce the silicate polymers of the present invention are sodium metasilicate anhydrous, sodium metasilicate pentahydrate, sodium sesquisilicate, sodium orthosilicate, and mixtures thereof.

The water-soluble silicate polymers of the invention may have a molecular weight distribution in the range of about 4,800 to about 2,000,000, preferably, about 13,000 to about 1,000,000, which distribution is unimodal and which is determined by gel-filtration, ultrafiltration, electrophoresis and the like. The degree of polymerization of the said silicate polymers is indicated in the range of about 75 to about 33,000, preferably about 210 to about 16,500, wherein the monomer unit is —($SiO_2$)—.

In embodiments for producing the silicate polymers of the present invention, a water-soluble silicate such as sodium orthosilicate, sodium metasilicate, potassium orthosilicate or potassium metasilicate, or a silicic acid containing material such as water glass is dissolved in an aqueous solution. Since said aqueous solution of the silicates has a high pH value, it is preferable to adjust the solution to pH 2–10, more preferably, pH 4–9.5, by the use of a conventional acid such as hydrochloric acid, sulfuric acid or acetic acid. It is desirable to add a saccharide carrier or diluent such as lactose, mannitol, sorbitol, sucrose, glucose, fructose, galactose, or mixtures thereof to the aqueous solution. A salt such as sodium chloride, potassium chloride or sodium sulfate may also be added to the solution.

Pharmaceutically effective water-soluble silicate polymers, methods for making and using them to treat diseases and medical conditions are disclosed in Japanese Patents 2,698,908 2,588,109, 2,727,441, 2,727,442, 2,948,784 and 3,113,619, and corresponding U.S. Pat. Nos. 5,534,509, 5,658,896, and 5,807,951 each to Konishi et al, the disclosures of which are each herein incorporated by reference in their entireties.

A crude drug extract obtained from animal, fungus or plant materials such as tanjin (Salvia militiorrhiza radix), shireisi (Ganoderma lucidum) and scouring rush (Equisetum hiemale) or an extract from inflammatory tissue inoculated with vaccinia virus contains the above water-soluble silicate polymers. Therefore, water-soluble silicate polymers purified or extracted from the extracts may be utilized as an ingredient of the composition of the present invention. The activity of the water-soluble silicate polymers contained in the extract may also be enhanced by addition of the saturated fatty acid to the crude drug or the extract.

Crude drug extracts which may be employed as a source of the water-soluble silicate polymers for use in the present invention are disclosed in copending U.S. application Ser. No. 09/200,918, for "CRUDE DRUG EXTRACTS, AND METHODS FOR MAKING AND STANDARDIZING SAME,"filed Nov. 30, 1998 in the name of Jin-emon Konishi, the disclosure of which is incorporated by reference in its entirety. As disclosed therein, the crude drug extracts contain not less than 0.05 mg of soluble silicon compounds calculated as silicon per gram of the dry crude drug. The crude drug extract may be obtained by extraction of various crude drugs, for example, animal and plant crude drugs including tanjin (*Salviae militiorrhizae* radix), shireishi (*Ganoderma lucidum*), creeping saxifrage (*Saxifraga stolonifera*), scouring rush (*Equisetum hiemale*), Chinese gutta percha, plantago herb, plantago seeds, chorei (polyporus sclerotium), saiko (bupleurum root), Japanese angelica root, elderberry, bukuryo (poria sclerotium), pueraria root, crude aloe, ginseng, ginger, alisma rhizome, schisandra fruit, sanshiti (root of *Panax nothoginseng*), jujube, chinpi (citrus unshiu peel), bakumondo (ophiopogon tuber), young staghorn, oriental bezoar, lumbicusa, bear bile, longgu, etc. The crude drug extracts may be obtained by extraction with water, ethanol or a suitable extracting solvent to which an additive such as phenol is added. At that time, extraction and concentration of the active substances may be enhanced by heating or changing the pH of the solvent. Thus, the following manufacturing methods may be exemplified for obtaining crude drug extracts as a source of water-soluble silicate polymers for use in accordance with the present invention:

1) Pure water is added to a crude drug material, the mixture is boiled with stirring and the insoluble matters are removed by filtration or the like to give an extract solution. The extract solution is concentrated if necessary and spray-dried or freeze-dried in vacuo to give a powder.

2) Pure water is added to a crude drug material, the mixture is boiled with stirring and the insoluble matters are removed by filtration or the like to obtain an extract. Pure water is further added to the residue, pH is adjusted to an alkaline region (to 8.5–10.5, for example to around 9.5), then the mixture is boiled with stirring again, and the insoluble matters are removed by filtration or the like to obtain an extract, and the extract is adjusted to about the neutral pH region and combined with the already-prepared first extract. Then, the combined extract is concentrated and/or evaporated to dryness if necessary to give a powder. Spray-drying or freeze-drying in vacuo to give a powder may be employed as in the above-mentioned method 1).

3) To a crude drug material is added a 1% aqueous phenol solution followed by boiling with stirring and the insoluble matters are removed by filtration or the like to give an extract solution. The extract solution is concentrated if necessary and spray-dried or freeze-dried in vacuo to give a powder.

4) Pure water and ethanol are added to a crude drug material, the mixture is boiled with stirring and the insoluble matters are removed by filtration or the like to give an extract solution. The extract solution is concentrated if necessary and spray-dried or freeze-dried in vacuo to give a powder.

5) After conducting the extracting operations as described in the above methods 1) to 4), the pH of the extract is adjusted to weakly alkaline (for example, to pH of around 8.5) followed by concentrating, and the pH of the concentrate is adjusted to nearly the neutral region followed by pulverizing in the same manner as mentioned above.

Conventional pH adjusting agents, such as inorganic or organic bases and acids and salts may be employed to obtain a desired pH for the extracting solvent and extract. For example, alkali metal hydroxides such as sodium hydroxide, and potassium hydroxide, etc. may be employed to obtain a desired alkaline pH. Exemplary acids which may be employed to adjust pH to the neutral range include hydrochloric acid, sulfuric acid, and hydrobromic acid, etc.

The crude drug extracts are characterized and evaluated for pharmaceutical effectiveness by specifying the soluble silicon compound content of the crude drug extract. The content of the soluble silicon compounds in the dried crude drug extract obtained by the above-mentioned manufacturing methods can be analyzed by the following method and is able to be regulated as an amount calculated as silicon.

Thus, the crude drug extract is added to water (to an extent of 1 mg/ml), the mixture is subjected to stirring and an ultrasonic treatment. In preferred embodiments, the stirring is conducted at room temperature for about ten minutes and ultrasonic treatment is conducted at room temperature for about ten minutes. Then, the insoluble matters are removed by filtration or centrifugation, and the amount of silicon in the resulting solution is measured by a molybdenum blue method. In addition, an inhibiting action of the same sample solution against the production of plasma kallikrein is measured and is confirmed as an index for the soluble silicon compounds. The measured inhibiting action against plasma kallikrein production may be employed as an index for the measurement and confirmation of the titer (potency of the biological activity) of the soluble silicon compounds having a biological activity.

In embodiments of the invention, extracts from an activated tissue which may be employed as a source of the water-soluble silicate polymers for use in the compositions and methods of the present invention may be extracts from inflammatory tissue inoculated with vaccinia virus disclosed in Japanese Examined Patent Publications Sho-63/039,572 B, Sho-63/025,600 B and Hei-03/043,279 B, Japanese Patent No. 2,594,222 and U.S. Pat. No. 5,013,558 to Konishi, U.S. Pat. No. 5,560,935 to Konishi, et al, and U.S. Pat. No. 6,051,613 to Ohno et al. The disclosures of Japanese Examined Patent Publications Sho-63/039,572 B, Sho-63/025,600 B and Hei-03/043,279 B, Japanese Patent No. 2,594,222, and U.S. Pat. Nos. 5,013,558 to Konishi, 5,560,935 to Konishi, et al. and 6,051,613 to Ohno et al are herein incorporated by reference in their entireties. A method for producing an extract from inflammatory tissue inoculated with vaccinia virus for use in the present invention is described, for example, in Example 1 of Japanese Examined Patent Publication Sho-63/039,572 B and Japanese Patent No. 2,594,222. Methods for producing extracts from inflammatory tissue inoculated with vaccinia virus for use in the present invention are also described, for example, in U.S. Pat. No. 5,013,558 to Konishi at column 1 line 44 to column 3 line 22, and in Examples 1 and 2 at column 3 lines 33 to 62, U.S. Pat. No. 5,560,935 to Konishi, et al. at column 2 line 55 to column 3 line 14, and column 3 line 33 to column 4 line 64, and in Examples 1 and 2 at column 5 line 6 to column 6 line 8, and U.S. Pat. No. 6,051,613 to Ohno at column 3 line 61 to column 6 line 24, and column 8 lines 6–29, which are herein incorporated by reference in their entireties.

A commercially available drug preparation of an extract from inflammatory rabbit skin inoculated with vaccinia virus is sold in Japan under the trade name Neurotropin by Nippon Zoki Pharmaceutical Co., Osaka, Japan. As mentioned at pages 1,927 and 1,928 of "Drugs in Japan, Ethical Drugs" ($22^{nd}$ edition, 1998–1999; edited by Japan Pharmaceutical Information Center; published by Yakugyo Jiho Co., Ltd.), this preparation is a drug containing non-proteinaceous active substances extracted and isolated from inflammatory rabbit skin inoculated with vaccinia virus. The preparation has been used for treatment of lower back pain, neck-shoulder-arm syndrome, periarthritis scapulohumeralis, arthrosis deformans, symptomatic neuralgia, post-herpetic neuralgia, pruritis due to dermatological diseases (such as eczema, dermatitis and urticaria), allergic rhinitis, and sequelae of subacute myelo-optico-neuropathy (such as coldness, pain and paresthesia/dysesthesia). It is available as an ethical drug in the form of injections (subcutaneous, intramuscular and intravenous) and tablets.

Neurotropin was used in an experimental study at the School of Medicine, University of California, Davis, to evaluate its influence on thymic microenvironmental abnormalities of New England black mice as reported by Y. Takeoka et al, *Int. J Immunotherapy*, XI(2), pp. 49–56 (1995). As taught by Takeoka et al, Neurotropin is a non-protein extract isolated from the inflamed dermis of rabbits inoculated with vaccinia virus and it has been reported in the literature as: 1) having beneficial effects on immune-depressed animals, 2) clinically useful as an analgesic and as an anti-allergy drug with few side-effects in humans, 3) improving the immune status of murine lupus in (NZB/NZW) F1 mice, and 4) inhibiting the development of EAE in Lewis rats, an autoimmune model of human multiple sclerosis.

The commercially available extract, Neurotropin, may be employed as a source for the water-soluble silicate polymer used in the compositions and methods of the present invention. The descriptions, properties and dosages of Neurotropin reported in the above-mentioned "Drugs in Japan, Ethical Drugs" and the Takeoka et al article are incorporated herein by reference in their entireties.

The physiologically active substance, i.e., an extract from inflamed skins inoculated with vaccinia virus, prepared as described in U.S. Pat. No. 5,560,935 may exhibit the following properties:
(1) Characteristic: an amorphous and hygroscopic powder with pale yellowish brown color containing 1–20 micrograms/mg (e.g. 2–10 micrograms/mg) of silicon components which are calculated as silicon;
(2) Solubility: it is soluble in water, methanol and ethanol and is insoluble in benzene and ether;
(3) pH: 6.0–8.3;
(4) Ultraviolet absorptions: max=265–275 nm;
(5) Color reactions: amino acid (positive to a ninhydrin reaction), saccharide (positive to an orcinol-iron(III) chloride-hydrochloric acid method), phosphorus (positive to a molybdenum blue method), protein (negative to a trichloroacetic acid method) and phenol (negative to a ferric chloride method).

The physiologically active substance, i.e., an extract from inflamed skins inoculated with vaccinia virus, prepared as described in U.S. Pat. No. 6,051,613 may exhibit the following properties:
(1) Appearance: Pale yellowish brown and hygroscopic powder.
(2) Solubility: Soluble in water, methanol and ethanol.

(3) Ultraviolet adsorption: λmax=255–275 nm.

(4) Ninhydrine reaction: Positive.

(5) One ml of perchloric acid is added to 2 mg of the extract of the present invention, and is heated until the solution become colorless. 3 ml of dilute hydrochloric acid, 0.4 g of amidol hydrochloride and 8 g of sodium hydrogen sulfite are dissolved in 100 ml of water, and then 2 ml of the resulting aqueous solution, 1 g of ammonium molybdate and 30 ml of water are mixed. 2 ml of the mixture is added to the above solution containing the extract of the present invention. Finally, the solution shows a blue color.

(6) 5 mg of the extract of the present invention is dissolved in 10 ml of water, 0.2 g of orcine and 0.135 g of iron(II)ammonium sulfate are dissolved in 5 ml of ethanol, 83 ml of hydrochloric acid is added to the mixture, and water is added until the total becomes 100 ml. 3 ml of the resulting mixture is added to 1 ml of the above solution containing the extract of the invention and heated in a boiling water bath. Finally, the solution shows a green color.

(7) Silver nitrate reagent is added to an aqueous solution of the extract of the present invention and a precipitate is produced.

(8) Contains nucleic acid bases.

(9) Various methods of protein detection are negative.

The inflamed or infected tissues may be animal tissues, organs or cultured cells inoculated or infected with vaccinia virus, a poxvirus.

In embodiments of the invention, a mixture of: a) one or more water-soluble silicate polymers obtained by polymerization, and b) one or more water-soluble silicate polymers obtained from an extract, such as an extract from inflammatory tissue inoculated with vaccinia virus, or a crude drug extract from a plant, animal or fungus, may be employed. For example, a bioactivating substance comprising a mixture of a water-soluble silicate polymer obtained by polymerization, and an extract from activated tissue may be employed, which bioactivating substance is disclosed in copending U.S. application Ser. No. 09/551,135, filed Apr. 17, 2000 in the name of Jin-emon Konishi for ":NOVEL BIOACTIVATING SUBSTANCE," the disclosure of which is herein incorporated by reference in its entirety. As disclosed therein, the bioactivating substance may comprise at least one silicon component and exhibits positive color reactions to amino acid (by a ninhydrin reaction), saccharide (by an orcinol-iron (III) chloride-hydrochloric acid method), phosphorus (by a molybdenum blue method) and silicic acid (by a molybdenum blue method), and negative qualitative reactions to protein (by a trichloroacetic acid method) and phenol (by a ferric chloride method), said bioactivating substance having a silicon component content which is more than 20 μg calculated as silicon per mg of dried substance.

For the purpose of manufacturing a pharmaceutical composition of the invention, an aqueous solution containing water-soluble silicate polymers is preferably dried to a powder. The powderization may be carried out according to a conventional method such as heating or lyophilization. To obtain a preferred powder, for example, the solution is dried by heating at 150° C. to 250° C. Also, a conventional lyophilization under reduced pressure may be used to powderize the solution. Powders of the water soluble silicate polymer in accordance with the present invention are storage stable for more than one year.

Compositions according to the present invention may comprise more than one water-soluble silicate polymer in the form of a mixture thereof.

To detect the production of silicate polymers, for example, a molybdenum blue coloration is measured. In this technique, a solution of ammonium molybdate is added to the aqueous solution of silicate, then sulfite solution is added to produce a blue coloration. The blue coloration is reduced as the polymerization of silicate proceeds. Also, the silicate polymers so produced can be separated by gel-filtration under acidic conditions at high molecular bands. An aliquot of this separated fraction is decomposed under alkali conditions to detect silicates by the molybdenum blue reaction.

The saturated fatty acid contained as an effective ingredient in the pharmaceutical composition of the present invention is a general name for a fatty acid having neither a double bond nor a triple bond in a molecule and is represented by the chemical formula $C_nH_{2n+1}COOH$. Preferably, it is a straight chain or branched chain saturated fatty acid having about 8 carbon atoms to about 26 carbon atoms. Exemplary of straight saturated fatty acids which may be employed are caprylic acid (8:0), capric acid (10:0), lauric acid (12:0), myristic acid (14:0), pentadecanoic acid (15:0), palmitic acid (16:0), heptadecanoic acid (17:0), stearic acid (18:0), icosanoic acid (20:0), heneicosanoic acid (21:0), docosanoic acid (22:0), tricosanoic acid (23:0), lignoceric acid (24:0) or cerotic acid (26:0). Exemplary of branched saturated fatty acids which may be employed are 2-hexyldecanoic acid, 13-methylpentadecanoic acid or 16-methylheptadecanoic acid.

Such a fatty acid may be used solely or as a mixture of plural fatty acids. The acid may be used either in a free form, or as a salt, such as a sodium salt and a potassium salt. Also, it is preferred to use the fatty acid in a water-soluble form. With regard to the saturated fatty acid and salt thereof, those which are commercially available may be used or those which are extracted and purified from animal fat or vegetable oil may be used. In embodiments of the present invention, the saturated fatty acid may be employed in the form of an aqueous solution of a fatty acid salt or an aqueous dispersion of a free fatty acid. In the present invention, the saturated fatty acid can be used in a weight ratio of from about 1:20 to about 50:1 times the total amount of the silicate polymers, calculated as silicon, preferably about 1:10 to about 30:1 times the total amount of silicate polymers, calculated as silicon.

The saturated fatty acid and water-soluble silicate polymer, effective ingredients of the present invention, can be formulated for various pharmaceutical compositions by combining with a suitable carrier or diluent for medical use. The pharmaceutical composition may be prepared by a conventional method as a form for parenteral administration such as subcutaneous, intravenous, intramuscular, rectal or nasal administration or a form for oral administration, for example, tablets, capsules, powders or liquids. In manufacturing such preparations, mixtures of each of the effective components may be used, e.g. a mixture of extracts containing water-soluble silicate polymers. Also, in manufacturing such preparations, the effective components may be combined with other suitable pharmaceutically active components. In the pharmaceutical compositions or formulations, the admixture of water-soluble silicate polymer and fatty acid components of the present invention may be used solely or together in pharmaceutically effective amounts with pharmaceutically effective amounts of other pharmaceutically active components for treating animals or humans.

In the case of injections, the both effective components may be made into a solution, suspension or emulsion in aqueous solvents such as distilled water for injection, physiological saline solution or glucose solution, or in nonaqueous solvents such as propylene glycol. If necessary, a conventional additive such as a solubilizing agent, isotonic agent, suspending agent, emulsifying agent, stabilizing agent or preservative may be added. The powders in a vial with aseptic treatment may be dissolved in said solution such as distilled water for injection, physiological saline solution or Ringer's solution just before using. Further, depending upon the state of the patient or the type of the disease, the components may be made into other preparation forms such as syrups, suppositories, inhalations, aerosols, eye drops or external preparations (ointments, gels or cataplasms) which are most suitable for the therapy.

In the case of preparations for oral use, the both components of the present invention may be made into tablets, diluted powders, granules or capsules with or without one or more suitable additives, for example, conventional fillers such as lactose, mannitol, corn starch, potato starch and calcium citrate, binders such as crystalline cellulose, cellulose derivatives (e.g. hydroxypropylcellulose), gum arabic, corn starch and gelatin, lubricants such as talc, extenders, moistening agents, buffering agents, stabilizing agents, preservatives, perfumes and the like.

In other embodiments, the polymeric silicate substances of the present invention may be mixed with at least one base material. The base material may be an oleaginous composition or fat/oil type material (e.g. cacao butter), an emulsifying base material, a water-soluble base material (e.g. Macrogol) or a hydrophilic base material, etc., to obtain a suppository.

A desired dose or a "pharmaceutically effective amount" of the effective components of the present invention may vary depending upon the patient to be treated (age, body weight or symptoms), preparation form, method of administration, period for administration, etc. In general 1 $\mu$g/kg to 10 mg/kg per day (calculated as silicate) may be given to an adult for achieving the desired pharmaceutical effect. In the case of parenteral administration such as injections, the desired dose may be ⅓ to ⅒ as large as an oral dose in general because of the difference in absorption rate. In the present invention, the saturated fatty acid can be used in a weight ratio of from about 1:20 to about 50:1 times the amount of the silicate polymers, calculated as silicon, preferably about 1:10 to about 30:1 times the amount of silicate polymers, calculated as silicon.

In a method of using the compositions of the present invention, the compositions are administered to a patient who has been diagnosed as having allergies and/or inflammation related to histamine release. Such patients are said to be "known to be in need of treatment" of a certain disease or condition involving histamine release, allergy or inflammation.

The following examples take place at room temperature and at atmospheric pressure, unless otherwise indicated. The following examples illustrate the present invention wherein all parts, percentages, ratios, and amounts are by weight and all temperatures are in ° C. unless otherwise indicated:

REFERENTIAL EXAMPLE 1

7.6 g of water glass (silicon; 1.2 g) was dissolved in 100 ml of water. 97.5 g of lactose was dissolved in 300 ml of water with heating. The water glass solution was mixed with the lactose solution, and then the pH was adjusted to 8.0 with diluted hydrochloric acid. The reaction mixture was dried at 200° C. to obtain 90 g of a powder. The resulting silicate polymers of the present invention have the following physical properties and contain 12 mg of silicon per 1 g of polymer:

Molecular weight distribution: 13,000 to 1,000,000

Degree of polymerization: 210 to 16,500

REFERENTIAL EXAMPLE 2

12.9 g of sodium metasilicate (silicon; 1.2 g) was dissolved in 100 ml of water. 95.8 g of lactose was dissolved in 300 ml of water with heating. The aqueous solution of sodium metasilicate was mixed with the lactose solution, and then the pH was adjusted to 8.0 with diluted hydrochloric acid. The reaction mixture was dried at 200° C. to obtain 90 g of a powder. The resulting silicate polymers of the present invention have the following physical properties and contain 12 mg of silicon per 1 g of polymer:

Molecular weight distribution: 15,000 to 900,000

Degree of polymerization: 250 to 15,000

REFERENTIAL EXAMPLE 3

5.9 g of sodium orthosilicate (silicon; 0.6 g) was dissolved in 100 ml of water. 99 g of mannitol was dissolved in 300 ml of water with heating. The aqueous solution of sodium orthosilicate was mixed with the mannitol solution, and then the pH was adjusted to 8.0 with diluted hydrochloric acid. The reaction mixture was dried at 200° C. to obtain 88 g of a powder. The resulting silicate polymers of the present invention have the following physical properties and contain 6 mg of silicon per 1 g of polymer:

Molecular weight distribution: 20,000 to 1,000,000

Degree of polymerization: 330 to 16,500

REFERENTIAL EXAMPLE 4

1.89 g of water glass (silicon; 0.3 g) was dissolved in 100 ml of water. 500 ml of 20% aqueous solution of lactose was added thereto, and then the pH was adjusted to 8.0 with diluted hydrochloric acid. Each 1.2 ml of the solution was pipetted into a vial and lyophilized. The resulting drypowdered silicate polymers of this invention have the following physical properties and contain 0.6 mg of silicon per vial:

Molecular weight distribution: 30,000 to 1,500,000

Degree of polymerization: 490 to 25,000

EXAMPLE 1

To perform the pharmacological test mentioned below, an aqueous solution of the fatty acid-containing composition of the present invention was prepared as follows. The saturated fatty acid used in the test was purchased from Wako Pure Chemical Industries and Tokyo Kasei Kogyo. A saturated fatty acid (20 mg) was weighed and sodium hydroxide (an aqueous solution of 1 mol/L) in an equimolar amount (or more if necessary) thereof and a physiological saline (or distilled water) were added thereto as a solvent to make the total volume 200 mL. The resulting solution (100 $\mu$g/mL) per se (original solution), or one as appropriately diluted with a physiological saline, was used for the test. Since the saturated fatty acid having a chain length of icosanoic acid or longer is hardly soluble, a solution having a concentration of 25 $\mu$g/mL was prepared and used as an original solution.

With regard to a water-soluble silicate polymer, 25 mg of the powder of the above-mentioned Referential Example 1 was weighed and placed into a vial and, for the purpose of measuring the activity of the said silicate polymer only, an original solution was prepared by dissolving it in 3 mL of a physiological saline and the solution was appropriately diluted with a physiological saline and used for the test. The composition of the present invention is comprised of a saturated fatty acid and a water-soluble silicate polymer. Accordingly, instead of a physiological saline, 3 mL of the above-mentioned original solution of a saturated fatty acid were added to a vial containing 25 mg of a water-soluble silicate polymer to form a solution that was used for the test as the original solution of the composition of the present invention in the same manner.

EXAMPLE 2

Suppressive Action to Histamine Release from Mast Cells (Degranulation-Suppressing Action)

Male Wistar rat (150–200 g) was exsanguinated by decapitation, 10 mL of MCM (Mast Cell Medium containing 150 mmol/L of NaCl, 3.7 mmol/L of KCl, 0.9 mmol/L of $CaCl_2$, 0.9 mmol/L of $MgCl_2$, 3.0 mmol/L of $Na_2HPO_4$, 3.5 mmol/L of $KH_2PO_4$, 5.6 mml/L of glucose and 0.1% gelatin; pH 6.8) containing 5 U/mL of heparin were injected intraperitoneally, massage was conducted for about 90 seconds and a celiotomy was carried out to collect a suspension of peritoneal exudation cells (PEC). The cells were centrifugally washed at 4° C. for 5 minutes at 130×g for three times and, finally, suspended in an appropriate amount of MCM to prepare a mast cell suspension ($1-2\times10^5$ cells/mL). The cell suspension (1 mL) and 0.5 mL of each test substance (the original solution or its appropriately diluted solution) were placed in a polyethylene tube, made to react at 37° C. for 10 minutes and further made to react for 10 minutes after addition of 0.5 mL of Compound 48/80, a histamine releaser, (final concentration: 50 mg/mL). After that, the tube was placed in an ice-cold water to stop the reaction and centrifuged at 4° C. for 5 minutes at 130×g and 1 mL of the supernatant was subjected to measurement of free histamine by a method of Shore, et al. (J. Pharm. Exp. Ther., 127, 183–186 (1959)). To 1 mL of another cell suspension were added each 0.5 mL of distilled water and 6% perchloric acid followed by mixing, the mixture was centrifuged (130×g) and 1 mL of the resulting supernatant was subjected to histamine measurement by the same way to determine the total histamine amount. The concentration of Compound 48/80 was determined as above to such an extent that about one-half of the total histamine amount was released.

An example of the result is shown below. The case where the degree of dilution was ¼ is the result when the original solution per se of the test substance was used (0.5 mL of the test substance solution/2 mL final volume of the test system). The action of the test substance for suppressing histamine release was shown by the value in terms of % of the control (a physiological saline only) where its histamine release value was defined as 100%. Mast cells are prepared at every test and, therefore, the sensitivity of the mast cells changes at each preparation. For example, since the cells prepared in the test of Table 3 have a very high sensitivity, the effects are observed at lower concentrations of the samples.

In the following Tables 1, 2 and 3, the phrase "S. E." refers to standard error, the phrase "V.S." means versus, and the variable "n" refers to the number of trials performed.

TABLE 1

Result: Fatty acid = Stearic acid (18:0)

Released Histamine Value = V.S. Control (% ± S.E., n = 3)

| Dilution Rate | Stearic Acid | Water-Soluble Silicate Polymer | Stearic Acid + Water-Soluble Silicate Polymer |
|---|---|---|---|
| 1/4 | 97.4 ± 2.52 | 40.4 ± 0.33 | 1.9 ± 0.96 |
| 1/10 | 93.0 ± 2.03 | 58.9 ± 0.57 | 17.4 ± 1.18 |
| 1/20 | 99.0 ± 0.87 | 70.5 ± 0.69 | 38.8 ± 1.47 |
| 1/50 | 106.7 ± 2.50 | 86.2 ± 0.81 | 78.9 ± 1.02 |

TABLE 2

Released Histamine Value = V.S. Control (% ± S.E., n = 3)

| Fatty Acid | Dilution Rate | Fatty Acid | Water-Soluble Silicate Polymer | Fatty Acid + Water-Soluble Silicate Polymer |
|---|---|---|---|---|
| Capric acid (10:0) | 1/4 | 94.5 ± 0.90 | 64.8 ± 0.85 | 49.5 ± 0.22 |
| Heptadecanoic acid (17:0) | 1/20 | 111.1 ± 2.87 | 70.5 ± 0.69 | 45.2 ± 1.48 |
| Icosanoic acid (20:0) | 1/10 | 102.2 ± 4.76 | 72.5 ± 1.40 | 4.3 ± 0.24 |
| Heneicosanoic acid (21:0) | 1/20 | 100.3 ± 4.99 | 69.7 ± 1.57 | 13.1 ± 0.35 |
| Docosanoic acid (22:0) | 1/20 | 99.1 ± 1.71 | 69.7 ± 1.57 | 6.4 ± 0.33 |
| Tricosanoic acid (23:0) | 1/10 | 97.8 ± 2.44 | 72.5 ± 1.40 | 3.3 ± 0.38 |

TABLE 3

Released Histamine Value = V.S. Control (% ± S.E., n = 3)

| Fatty Acid | Dilution Rate | Fatty Acid | Water-Soluble Silicate Polymer | Fatty acid + Water-Soluble Silicate Polymer |
|---|---|---|---|---|
| Stearic acid (Straight chain, 18:0) | 1/100 | 100.2 ± 4.37 | 80.1 ± 1.80 | 24.5 ± 4.68 |
| The same as above | 1/200 | 101.6 ± 1.67 | 90.9 ± 2.80 | 50.2 ± 1.79 |
| 2-Hexyldecanoic acid (Branched chain, 16:0) | 1/100 | 81.4 ± 0.94 | 80.1 ± 1.80 | 28.6 ± 0.18 |
| The same as above | 1/200 | 102.0 ± 1.18 | 90.9 ± 2.80 | 65.8 ± 3.82 |
| 13-Methyl-pentadecanoic acid (Branched chain, 16:0) | 1/100 | 101.9 ± 0.97 | 80.1 ± 1.80 | 67.0 ± 0.69 |

TABLE 3-continued

| | | Released Histamine Value = V.S. Control (% ± S.E., n = 3) | | |
|---|---|---|---|---|
| Fatty Acid | Dilution Rate | Fatty Acid | Water-Soluble Silicate Polymer | Fatty acid + Water-Soluble Silicate Polymer |
| 16-Methyl-heptadecanoic acid (Branched chain, 18:0) | 1/50 | 106.4 ± 1.68 | 63.4 ± 1.68 | 45.9 ± 1.33 |
| The same as above | 1/100 | 111.5 ± 1.13 | 80.1 ± 1.80 | 66.8 ± 3.41 |

As apparent from the results of the above pharmacological tests, saturated fatty acids show nearly no suppressive action to histamine release from mast cells. As shown in Table 1, a water-soluble silicate polymer had a suppressive action to histamine release dose-dependently and, when it was combined with a saturated fatty acid, the action was very much increased. A mast cell contains histamine-containing granules and its degranulation is induced by anaphylatoxins such as complement component C3a and C5a or by a chemical compound such as Compound 48/80 in addition to a cross-linking reaction of IgE receptors. In consequence, histamine is released outside from the cell and allergic reaction is induced. Thus, a structural change takes place in the cell membrane of the mast cell by such inducing substances whereupon histamine is released and it is believed that the composition of the present invention has a protective action against such changes in the cell membrane. The cell is a fundamental unit of a living body and damage to the cell by external and internal stimulation or stress induces allergy and inflammation. The composition of the present invention has an excellent organism maintaining function for preventing cell damage. Accordingly, the composition of the present invention is useful as a therapeutic or preventive agent in treating diseases in which histamine participates such as allergy and inflammation.

What is claimed is:

1. A pharmaceutical composition comprising:
   a saturated fatty acid, and
   a pharmaceutically effective amount of a water-soluble silicate polymer, wherein said water-soluble silicate polymer has a molecular weight distribution in the range of about 4,800 to about 2,000,000, as determined by gel-filtration chromatography, and has a degree of polymerization in the range of about 75 to about 33,000, and
   wherein the saturated fatty acid is present in a weight ratio of from about 1:20 to about 50:1 times the amount of the water-soluble silicate polymer, calculated as silicon.

2. A pharmaceutical composition according to claim 1 which is effective as an anti-allergy agent or as an anti-inflammatory agent.

3. A pharmaceutical composition according to claim 1 which further comprises a saccharide crier or diluent.

4. A pharmaceutical composition according to claim 1 wherein the saturated fatty acid comprises a straight or branched saturated fatty acid having about 8 to about 26 carbons.

5. A pharmaceutical composition according to claim 1 which is ma form for parenteral administration selected from the group consisting of subcutaneous, intravenous, intramuscular, rectal and nasal administration, or which is in a form for oral administration selected from the group consisting of tablets, capsules, powders and liquids.

6. A pharmaceutical composition according to claim 1 which is effective to suppress histamine release from mast cells.

7. A pharmaceutical composition according to claim 1 wherein the degree of polymerization of said silicate polymer is in the range of about 210 to about 16,500.

8. A pharmaceutical composition according to claim 1 which is in an injectable form comprising a solution, suspension or emulsion in an aqueous solvent or in a nonaqueous solvent.

9. A method for enhancing the pharmacological activity of a water-soluble silicate polymer comprising mixing a pharmaceutically effective amount of a water-soluble silicate polymer with a saturated fatty acid,
   wherein said water-soluble silicate polymer has a molecular weight distribution in the range of about 4,800 to about 2,000,000, as determined by gel-filtration chromatography, and has a degree of polymerization in the range of about 75 to about 33,000, and
   wherein the saturated fatty acid is mixed with the water-soluble silicate polymer in a weight ratio of from about 1:20 to about 50:1 times the amount of the water-soluble silicate polymer, calculated as silicon.

10. A method for enhancing the pharmacological activity of a water-soluble silicate polymer according to claim 9 wherein said water-soluble silicate polymer is in the form of a storage stable powder.

11. A method for enhancing the pharmacological activity of a water-soluble silicate polymer according to claim 9 wherein the pharmacological activity enhanced is anti-allergy activity or anti-inflammatory activity.

12. A method fin enhancing the pharmacological activity of a water-soluble silicate polymer according to claim 10 wherein said storage stable powder is obtained by providing an aqueous solution containing a water-soluble silicate polymer and a saccharide carrier or diluent, and the aqueous solution is dried to a storage stable powder.

13. A method for enhancing the pharmacological activity of a water-soluble silicate polymer according to claim 9, wherein the saturated fatty acid comprises an aqueous solution of a fatty acid salt or an aqueous dispersion of a free fatty acid.

14. A method for enhancing the pharmacological activity of a water-soluble silicate polymer according to claim 10, wherein the saturated fatty acid comprises an aqueous solution of a fatty acid salt or an aqueous dispersion of a free fatty acid.

15. A method for enhancing the pharmacological activity of a water-soluble silicate polymer according to claim 9 wherein the saturated fatty acid comprises a straight chain or branched chain saturated fatty acid having about 8 carbon atoms to about 26 carbon atoms.

16. A method for enhancing the pharmacological activity of a water-soluble silicate polymer according to claim 9 wherein the degree of polymerization of said silicate polymer is in the range of about 210 to about 16,500.

17. A pharmaceutical composition, comprising:
a potassium or sodium salt of a saturated fatty acid, and
a pharmaceutically effective amount of a water-soluble silicate polymer, wherein said water-soluble silicate polymer has a molecular weight distribution in the range of about 4,800 to about 2,000,000, as determined by gel-filtration chromatography, and has a degree of polymerization in the range of about 75 to about 33,000, and
wherein the potassium or sodium salt of a saturated fatty acid is present in a weight ratio of from about 1:20 to about 50:1 times the amount of the water-soluble silicate polymer, calculated as silicon.

18. A pharmaceutical composition according to claim 1, wherein the water-soluble silicate polymer is prepared by polymerization of a silicic acid selected from the group consisting of orthosilicic acid, metasilicic acid, mesodisilicic acid, mesotrisilicic acid, and mesotetrasilicic acid.

19. A pharmaceutical composition according to claim 1, wherein the water-soluble silicate polymer is prepared by polymerization of a silicate selected from the group consisting of silicate sodium metasilicate anhydrous, sodium metasilicate pentahydrate, sodium sesquisilicate, sodium orthosilicate, and mixtures thereof.

20. A pharmaceutical composition according to claim 1, wherein the water-soluble silicate polymer is prepared from water glass.

21. A pharmaceutical composition according to claim 4, wherein the saturated fatty acid is selected from the group consisting of caprylic acid, capric acid, lauric acid, myristic acid, pentadecanoic acid, palmitic acid, heptadecanoic acid, stearic acid, icosanoic acid, heneicosanoic acid, docosanoic acid, tricosanoic acid, lignoceric acid, cerotic acid, 2-hexyldecanoic acid, 13-methylpentadecanoic acid, 16-methylheptadecanoic acid, and mixtures thereof.

22. A pharmaceutical composition according to claim 4, wherein the saturated fatty acid is selected from the group consisting of stearic acid, 2-hexyldecanoic acid, 13-methylpentadecanoic acid, and 16-methylheptadecanoic acid.

23. A pharmaceutical composition according to claim 1, wherein the saturated fatty acid is water-soluble.

24. A method for enhancing the pharmacological activity of a water-soluble silicate polymer comprising mixing a pharmaceutically effective amount of a water-soluble silicate polymer with a potassium or sodium salt of a saturated fatty acid,
wherein said water-soluble silicate polymer has a molecular weight distribution in the range of about 4,800 to about 2,000,000, as determined by gel-filtration chromatography, and has a degree of polymerization in the range of about 75 to about 33,000, and wherein the potassium or sodium salt of a saturated fatty acid is present in a weight ratio of from about 1:20 to about 50:1 times the amount of the water-soluble silicate polymer, calculated as silicon.

25. A method according to claim 9, wherein the histamine suppression of the water-soluble silicate polymer is increased.

26. A method according to claim 15, wherein the saturated fatty acid is selected from the group consisting of caprylic acid, capric acid, lauric acid, myristic acid, pentadecanoic acid, palmitic acid, heptadecanoic acid, stearic acid, icosanoic acid, heneicosanoic acid, docosanoic acid, tricosanoic acid, lignoceric acid, cerotic acid, 2-hexyldecanoic acid, 13-methylpentadecanoic acid, 16-methylheptadecanoic acid, and mixtures thereof.

27. A method according to claim 15, wherein the saturated fatty acid is selected from the group consisting of stearic acid, 2-hexyldecanoic acid, 13-methylpentadecanoic acid, and 16-methylheptadecanoic acid.

* * * * *